(12) United States Patent
Antkowiak et al.

(10) Patent No.: US 7,405,262 B2
(45) Date of Patent: Jul. 29, 2008

(54) PREPARATION OF FUNCTIONALIZED ANIONIC POLYMERIZATION INITIATORS

(75) Inventors: Thomas Antkowiak, Rittman, OH (US); Christine Rademacher, Akron, OH (US); Anthony Ramic, Parma, OH (US); David F. Lawson, Uniontown, OH (US)

(73) Assignee: Bridgestone Corporation, Chuo-ku, Tokyo (JP)

( * ) Notice: Subject to any disclaimer, the term of this patent is extended or adjusted under 35 U.S.C. 154(b) by 0 days.

(21) Appl. No.: 10/520,989

(22) PCT Filed: Jul. 11, 2003

(86) PCT No.: PCT/US03/21871

§ 371 (c)(1),
(2), (4) Date: Jan. 10, 2005

(87) PCT Pub. No.: WO2004/007563

PCT Pub. Date: Jan. 22, 2004

(65) Prior Publication Data

US 2006/0036050 A1 Feb. 16, 2006

Related U.S. Application Data

(60) Provisional application No. 60/395,085, filed on Jul. 11, 2002.

(51) Int. Cl.
*C08F 4/46* (2006.01)
*C07F 1/02* (2006.01)
*C08F 236/10* (2006.01)

(52) U.S. Cl. .......... 526/173; 526/176; 526/178; 526/179; 526/180; 526/181; 502/155; 502/157; 260/665 R; 544/106; 544/358; 546/152; 548/578; 556/87; 556/465; 564/336; 568/17; 568/38; 568/77; 562/899

(58) Field of Classification Search .......... 526/173, 526/178, 180, 181, 182, 176, 179; 502/155, 502/157; 260/665 R; 544/106, 358; 546/152; 548/578; 556/87, 465; 562/899; 564/336; 568/17, 38, 77
See application file for complete search history.

(56) References Cited

U.S. PATENT DOCUMENTS

| 3,326,881 | A |   | 6/1967  | Uraneck et al.          |
|-----------|---|---|---------|--------------------------|
| 3,439,049 | A | * | 4/1969  | Trepka ............ 568/784 |
| 3,725,368 | A | * | 4/1973  | Morrison et al. ...... 526/180 |
| 3,862,251 | A | * | 1/1975  | Strecker .......... 260/665 R |
| 4,497,748 | A | * | 2/1985  | Vitus et al. ........ 260/665 R |
| 4,861,742 | A | * | 8/1989  | Bronstert et al. ....... 502/157 |
| 5,496,940 | A |   | 3/1996  | Lawson et al.           |
| 5,523,364 | A |   | 6/1996  | Engel et al.            |
| 5,527,753 | A |   | 6/1996  | Engel et al.            |
| 5,550,203 | A |   | 8/1996  | Engel et al.            |
| 5,567,815 | A | * | 10/1996 | Hall et al. ............ 540/541 |
| 5,574,109 | A |   | 11/1996 | Lawson et al.           |
| 5,786,441 | A |   | 7/1998  | Lawson et al.           |
| 5,932,662 | A |   | 8/1999  | Lawson et al.           |

FOREIGN PATENT DOCUMENTS

EP 0693505 A1 1/1996

* cited by examiner

*Primary Examiner*—Fred M Teskin
(74) *Attorney, Agent, or Firm*—Arthur M. Reginelli; Meredith E. Hooker

(57) ABSTRACT

A process for preparing a functionalized polymerization initiator, the process comprising combining a functionalized styryl compound and an organolithium compound.

22 Claims, No Drawings

PREPARATION OF FUNCTIONALIZED ANIONIC POLYMERIZATION INITIATORS

This application is the national stage of International Application No. PCT/US03/21871, filed on Jul. 11, 2002, which claims the benefit of U.S. Provisional Application No. 60/395,085, filed on Jul. 11, 2002.

FIELD OF THE INVENTION

This invention relates to novel processes for preparing functionalized lithium compounds that are useful as initiators for anionic polymerizations.

BACKGROUND OF THE INVENTION

Conjugated diene monomers are often anionically polymerized by using alkyllithium compounds as initiators. Selection of certain alkyllithium compounds can provide a polymer product having a functionality at the head of the polymer chain. The ability to head-functionalize anionically-polymerized polymers has provided many advantages to tire technology. For example, lithiated cyclic amines, such as lithio hexamethyleneimine, has been employed to initiate the polymerization of conjugated dienes, as well as the copolymerization of conjugated dienes and vinyl aromatic monomers, to produce polymers having a cyclic-amine head functionality. These polymers have proven to provide technologically useful tire treads that are characterized by improved traction, low rolling resistance, and improved wear.

The synthesis of these polymers is advantageously conducted in environmentally friendly solvents such as technical hexanes. The high temperatures at which some polymerizations occur, however, has led to the problem of reduced head functionality. To alleviate this problem, it was discovered that the use of cyclic aminoalkyllithium compounds, such as hexamethyleneimine propyllithium, could withstand high polymerization temperatures and thereby lead to polymers having greater functionality.

The preparation of these cyclic aminoalkyllithium compounds, however, has proven to be difficult and inefficient. In one technique, the initiators are prepared by reacting a cyclic aminoalkyllithium halide with elemental lithium or an organolithium compound. Where the halide is reacted with elemental lithium, the product must be separated from byproducts such as lithium metal and lithium chloride mud. Separation of these products can prove difficult, in part due to the limited solubility of the aminoalkyllithiums. Additionally, the product made by this route is often contaminated with undesirable side products such as the products of Wurtz coupling. Moreover, the precursor aminoalkylhalide compounds are capable of self-quaternization, thus consuming the reactive halide. As a result, it is necessary to store these compounds at low temperatures or as their hydrohalide salts and liberate the aminoalkylhalide by treatment with base a short time before lithiation is carried out. When the halide is reacted with an organolithium compound, the reaction inefficiently requires two or more equivalents of lithium from the organolithium to prevent undesirable side reactions that occur between the lithiated amine and the resultant chlorinated organic byproducts.

Because cyclic aminoalkyllithium compounds remain useful as initiators for preparing functionalized polymers, there is a need to overcome the problems associated with the synthesis of these initiators.

SUMMARY OF THE INVENTION

In general the present invention provides a process for preparing a cyclic-aminoalkyllithium anionic polymerization initiator, the process comprising combining a functionalized styryl compound and an organolithium compound.

The present invention further includes an anionic polymerization initiator defined according to the formula I

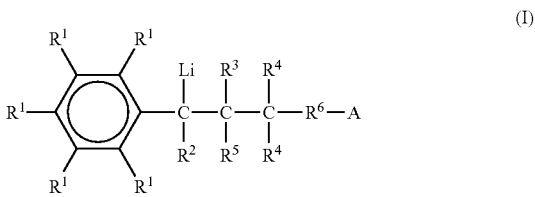

where each $R^1$ is independently hydrogen or a hydrocarbyl group, $R^2$ is hydrogen or a hydrocarbyl group, $R^3$ is hydrogen or a hydrocarbyl group, each $R^4$ is independently hydrogen or a monovalent hydrocarbyl, $R^5$ is hydrogen or a hydrocarbyl group, where at least one of $R^3$ or $R^5$ is hydrocarbyl, $R^6$ is a covalent bond or a hydrocarbylene group, and A is a functional group.

The present invention still further provides a polymer prepared by a process comprising the steps of polymerizing monomer with an initiator that is prepared by combining a functionalized styryl compound and an organolithium compound.

Novel aminoalkyllithium initiators can now be prepared by reacting an organolithium compound with functionalized styryl derivatives that contain cyclic amine functionalities. Advantageously, this discovery not only solves problems associated with the prior art preparation of cyclic aminoalkyllithiums compounds, but this discovery has also provided a method whereby a host of functionalized initiators can be prepared by lithiating numerous functionalized styryl derivatives. This lithiation proceeds by way of an addition reaction, which thereby avoids by-products that result from substitution reactions of the halo alkyl precursors with lithium or lithium-containing compounds and avoids the need to liberate or treat the quaternized base. Further, because the addition reaction to the functionalized styryl derivatives occurs at a location between the amine and phenyl substituents of the styryl derivative, the reaction provides a highly stabilized carbon-lithium site.

Also, where the functionalized styryl derivative is prepared by a substitution reaction in lieu of an addition reaction, the process has been found to be more efficacious because less starting material is lost to the formation of undesirable side-products. The resultant aminoalkyllithium initiators can advantageously be used to prepare polymers that include a functional group at the head of the polymer.

DETAILED DESCRIPTION OF ILLUSTRATIVE EMBODIMENTS

The novel functionalized lithium-containing anionic polymerization initiators of this invention are uniquely prepared by combining functionalized styryl reagent with an organolithium reagent.

This initiator can be represented by the formula I

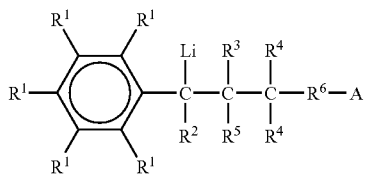

(I)

where each $R^1$, $R^2$, $R^3$, $R^4$, and $R^5$ is independently hydrogen or a hydrocarbyl group, where at least one of $R^3$ or $R^5$ are hydrocarbyl, $R^6$ is a covalent bond or a hydrocarbylene group, and A is a functional group.

The hydrocarbyl groups include, but are not limited to, alkyl, cycloalkyl, substituted cycloalkyl, alkenyl, cycloalkenyl, substituted cycloalkenyl, aryl, allyl, substituted aryl, aralkyl, alkaryl, and allynyl groups, with each group preferably containing from 1 carbon atom, or the appropriate minimum number of carbon atoms to form the group, up to 20 carbon atoms. These hydrocarbyl groups may contain heteroatoms such as, but not limited to, nitrogen, oxygen, silicon, sulfur, and phosphorus atoms.

The hydrocarbylene groups include, but are not limited to, alkylene, cycloalkylene, substituted alkylene, substituted cycloalkylene, alkenylene, cycloalkenylene, substituted alkenylene, substituted cycloalkenylene, arylene, and substituted arylene groups, with each group preferably containing from 1 carbon atom, or the appropriate minimum number of carbon atoms to for the group, up to 20 carbon atoms. These hydrocarbylene groups may contain heteroatoms such as, but not limited to, nitrogen, oxygen, silicon, sulfur, and phosphorus atoms.

Advantageously, numerous functional groups can be selected based on the ultimate application of the polymer that will be synthesized with the initiator. Exemplary functional groups include amine groups, phosphine groups, ether groups, thio ether groups, seleno groups, silyl groups, alkyl tin groups, and short-chain thermoplastic polymer segments.

Useful amine groups include those defined by the Formula II

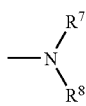

(II)

where each $R^7$ and $R^8$ is independently a hydrocarbyl group or where $R^7$ and $R^8$ join to form a hydrocarbylene group. Preferably, neither $R^7$ nor $R^8$ is hydrogen or includes a protonated heteroatom or carbonyl group.

In one embodiment, the hydrocarbyl groups $R^7$ and $R^8$ join together to form a hydrocarbylene group, which results in a cyclic amine that can be represented by the Formula III

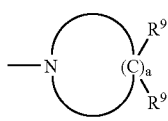

(III)

where each $R^9$ is independently hydrogen or a hydrocarbyl group, or where each $R^9$ join together to form a hydrocarbylene group, which results in a bicyclic compound, and where a is an integer from 4 to about 18. In fact, the substituents of formula II can include multi-cyclo substituents such as tricyclo substituents.

Specific examples of cyclic amine groups include -pyrrolidine, -3-methypyrrolidine, -3,4dimethylpyrrolidine, -3,3-dimethylpyrrolidine, -piperidine, -4-methylpiperidine, -3-methylpiperidine, -morpholine, -4-methylpiperazine, -4-ethyl-piperazine, -4-propylpiperazine, -hexamethyleneimine (or -perhydroazepine), -trimethylperhydroazepine, -azacyclotridecane, -azacyclohexadecane, -azacycloheptadecene, -trimethylazabicyclooctane, -perhydroisoquinoline, and -perhydroindole.

In another embodiment, at least one hydrocarbyl group is a cyclic hydrocarbyl group such as a cyclopentane group, a cyclohexane group, a cycloheptane group, and the like. In one particular embodiment, the cyclic hydrocarbyl group includes a hetero atom such as, but not limited to, nitrogen. This cyclic hydrocarbyl group results in a functional group that can be defined, for example, by the formula IV

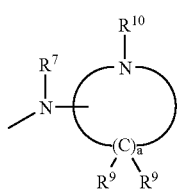

(IV)

where $R^7$ and $R^9$ are as defined above, and $R^{10}$ is a hydrocarbyl group.

In another embodiment, preferred hydrocarbyl groups (i.e., $R^7$ and $R^8$) may include aromatic groups such as, but not limited to, benzene, pyridine, thiophene, furan, N-methylpyrrole and selenophene groups. Other aromatic groups include polynuclear groups such as, but not limited to pyrene, anthracene and naphthalene.

In another embodiment, the hydrocarbyl group may include a silyl group (e.g., —$SiR_3$) where R is a hydrocarbyl group as defined above.

Useful phosphine groups include those defined by the formula V

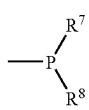

(V)

where each $R^7$ and $R^8$ is independently a hydrocarbyl group as defined above. Because the phosphine groups are similar in valance to the amine groups, groups that are analogous to the amine groups defined above are useful. Examples of phosphine groups include diphenyl phosphine.

Useful ether groups can be defined by the formula VI

—O—$R^7$ (VI)

where $R^7$ is a hydrocarbyl group as defined above. One Example of an ether group includes those where $R^7$ is aromatic, such as

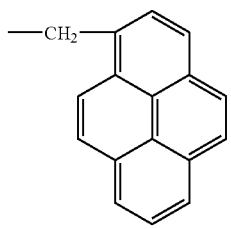

Useful thioether and seleno ether groups can be defined by the respective formulas VII and VIII

 (VII)

 (VIII)

where $R^7$ is a hydrocarbyl group as defined above. Because the thio ether and seleco ether groups are similar in valence to the ether groups, groups that are analogous to the ether groups are useful.

Examples of thio ether groups include t-butyl thio ether.

Silyl groups include those defined by the formula IX

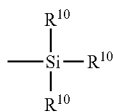 (IX)

where $R^{10}$ is a hydrocarbyl group or an alkoxy group.

Examples of silyl groups include trimethyl silyl, triethyl silyl, dimethoxy methyl silyl, and dimethyl methoxy silyl.

While numerous functional groups can be employed, one preferred type of functional group include those groups that interact or react with rubber fillers. Functional groups that will react or interact with rubber fillers include strong, weak, or selective functional groups. Strong functional groups include those substituents that undergo some type of bonding with the filler, e.g., covalent or ionic bonding. Weak functional groups include those groups that interact with filler via through-space interaction, e.g., H-bonding or van der Waals interaction, as well as those groups that interact or attract to each other and thereby form a domain within the rubber matrix of the polymer. Selective functional groups include those groups whose affinity toward filler particles or rubber can be activated after processing, e.g., during cure. Examples of selective functional groups include those described in U.S. Pat. No. 6,579,949, which is incorporated herein by reference.

Functional groups that are filler interactive include, but are not limited to, cyclic amines, alkyl amines, alkyl tins, and trialkoxy silanes.

The initiator of this invention is uniquely synthesized by combining a functionalized styryl reagent with an organolithium reagent.

The functionalized styryl reagent and the organolithium can be reacted in a 1:1 molar ratio, although an excess of either reagent can be employed. In a preferred embodiment, an excess of the organolithium is employed (e.g., 1 mole of organolithium to 0.9 moles of the functionalized styryl).

This reaction can take place by contacting the functionalized styryl and the organolithium under ambient conditions within an inert solvent. This reaction can also take place in the presence of monomer. In one embodiment, the initiator is prepared in situ whereby the reaction between the functionalized styryl reagent and the organolithium compound occurs in the presence of monomer that is intended to form the main chain of the resultant polymer.

The reaction preferably takes place in an organic solvent including anhydrous or non-polar polar solvents and hydrocarbon solvents. The reaction conditions are preferably the same as those that are conventionally employed when organolithium (e.g., n-butyllithium) is used to initiate and anionic polymerization of conjugated dienes.

The functionalized styryl reagent can be defined by formula X:

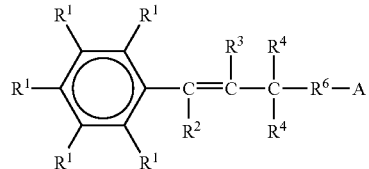 (X)

where each $R^1$, $R^2$, $R^3$, $R^4$, $R^6$ and A are as defined as above.

In one embodiment, preferred functionalized styryl reagent is a cyclic-amino functionalized styryl reagent, which can be defined by the formula XI:

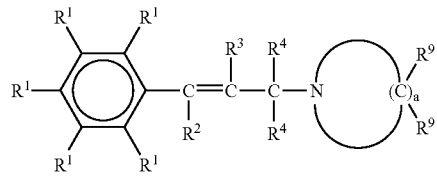 (XI)

where each $R^1$, $R^2$, $R^3$, $R^4$, and $R^9$, and a is defined above. Preferably, each $R^1$ is a hydrogen atom or an alkyl group including 1 to about 6 carbon atoms, $R^2$ is a hydrogen atom, an alkyl group containing 1 to about 6 carbon atoms, or a phenyl group, $R^3$ is a alkyl group containing 1 to about 6 carbon atoms, each $R^4$ is a hydrogen atom or an alkyl group containing 1 to about 6 carbon atoms, each $R^9$ is hydrogen or an alkyl group including about 1 to about 6 carbon atoms, and a is an integer from about 4 to about 12.

Some specific examples of the cyclic-amino functionalized styryl compounds include N-(cinnamyl): -pyrrolidine, -3-methypyrrolidine, -3,4-dimethylpyrrolidine, -3,3-dimethylpyrrolidine, -piperidine, -4-methylpiperidine, -3-methylpiperidine, -morpholine, -4-methlpiperazine, -4-ethyl-piperazine, -4-propylpiperazine, -hexamethyleneimine (or -perhydroazepine), -trimethylperhydroazepine, -azacyclotridecane, -azacyclohexadecane, -azacycloheptadecene, -trimethylazabicyclooctane, -perhydroisoquinoline, and -perhydroindole.

In one embodiment, the functionalized styryl reagent can be prepared by reacting a reactive styryl reagent with a functionalized nucleophile that is not reactive toward or less reactive toward the active double bond (i.e., won't add to the double bond) of the reactive styryl reagent than toward the carbon bearing the leaving group of the reactive styryl reagent. For example, the preferred cyclic-amino functionalized styryl reagent can be prepared by reacting a reactive styryl reagent (e.g., cinnamyl chloride) with a cyclic amine (e.g., hexamethylene imine) via substitution of an allylic halide.

Alternatively, this can be accomplished via a coupling of an allylic alcohol. For example, a styryl amino compound can be formed by the reaction of a cyclic secondary amine with cinnamyl alcohol in the presence of tin dichloride and a palladium(0) catalyst. Styryl amino compounds can also be formed via the displacement of halogen from a cinnamyl halide that is treated with a secondary cyclic amine. An excess of the same amine, another amine, or another base can be used as a proton scavenger.

In this embodiment, the reactive styryl reagent can be defined by formula XII:

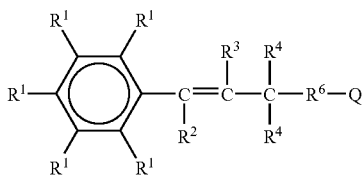

(XII)

where each $R^1$, $R^2$, $R^3$, $R^4$, and $R^6$ is defined as above, and Q is a leaving group. Exemplary leaving groups include halides, ester groups, alkyl or aryl sulfonates, and carboxylates.

Those skilled in the art can envision numerous functionalized nucleophile that can be reacted with the reactive styryl compound to form the functionalized styryl reagent. Examples of functionalized nucleophile include cyclic amines, alkylamines, functionalized alcohols, functionalized thiols, functionalized selenols, and the metal salts thereof.

The preferred cyclic amine can be defined by the formula XIII:

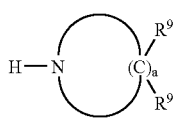

(XIII)

where each $R^6$ and a are defined as above. Useful cyclic amines include pyrrolidine, piperidine, 3-methylpiperidine, 4-alkylpiperazine such as 4-propylpiperazine, perhydroazepine, which is also known as hexamethyleneimine, 1-azacyclooctane, perhydroisoquinoline, or perhydroindole.

It is believed that the cyclic amine will displace the leaving group, and the nitrogen atom will bond with or via $R^5$ in a nucleophilic substitution reaction.

In another embodiment, the functionalized nucleophile is not reactive toward or less reactive toward the active double bond (i.e., won't add to the double bond) of the reactive styryl reagent than toward the carbon bearing the leaving group of the reactive styryl reagent.

For example, the reactive styryl reagent can be reacted with a polymer having an —OLi group at its tail to form a functionalized styryl reagent. Those skilled in the art appreciate that a polymer having an —OLi at its tail can be prepared by terminating a living polymer with an epoxide. Where the living polymer is initiated with a functionalized initiator such as a cyclic amine or a cyclic amino lithium or a trialkyltin lithium, the resulting functionalized stryl reagent will include the cyclic amino or trialkyltin group as a functional group.

In this embodiment, the preparation of the functionalized styryl reagent can be carried out by reacting one mole of the reactive styryl reagent with one mole of the functionalized nucleophile (e.g., cyclic amine) and one mole of a scavenging or non-nucleophilic base. Those skilled in the art will appreciate that the functionalized nucleophile (e.g., cyclic amine) can act as the scavenging or non-nucleophilic base, and therefore two moles of the functionalized nucleophile (e.g., cyclic amine) should be employed per mole of the reactive styryl compound in the situation where a separate base is not employed. As in other embodiments, an excess of any of the reactants may be employed, although an excess of cinnamyl halide is not recommended.

In another embodiment, the functionalized styryl reagent is prepared by reacting a reactive styryl reagent with a functionalized electrophile. In this embodiment, the reactive styryl reagent can be defined by the formula XIV

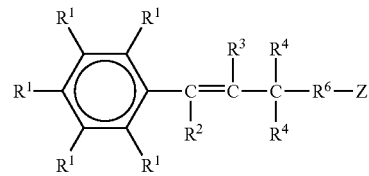

(XIV)

where each $R^1$, $R^2$, $R^3$, $R^4$, and $R^6$ is defined as above, and Z is a nucleophile. Examples of nucleophiles include hydroxyl groups, primary or secondary amines, thiogroups, or the metal salts thereof.

Examples of functionalized electrophiles include aminoalkyl halides, silyl halides, and reactive vinyl ethers (e.g., dihydropyran). As with the previous embodiments, this reaction is preferably accomplished by reacting a 1:1 molar ratio of the reactive styryl reagent with the functionalized electrophile, although an excess of either compound may be used. As those skilled in the art will appreciate, this reaction may preferably proceed in the presence of catalysts or scavengers.

Useful organolithium reagents can be defined by the formula $R^{11}Li$, where $R^{11}$ is a hydrocarbyl group as defined above. The preferred hydrocarbyl groups are alkyl groups containing 1 to about 6 carbon atoms. The preferred organolithium compound is n-butyllithium, which is readily commercially available.

In one embodiment, the initiator is prepared in the presence of a small amount of monomer, (e.g., from about 2 to about 30 moles of monomer/mmol of lithium) outside the presence of the majority of the monomer to be polymerized; i.e., monomer other than that which is intended to form the main chain of the resultant polymer. Or, the monomer is added a very short time after the organolithium reagent is added to the functionalized styryl compound. In this embodiment, the resultant initiator will include a chain-extended substituent. This initiator can be represented by the formula XV

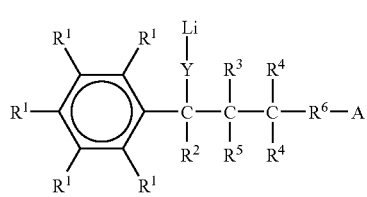

(XV)

where each $R^1$, $R^2$, $R^3$, each $R^4$, $R^5$, $R^5$, and A are as defined as above, and Y represents a chain-extended segment that results from the polymerization of the small amount of monomer present during the formation of the initiator. In preferred embodiments, the segment Y will include from about 3 to about 20 units deriving from the monomer.

Polymerizations that employ the initiator prepared according to this invention may be employed within batch processes, continuous processes, metered batch process, or semi-continuous processes. The preferred polymerization methods employ the chain extended initiator inasmuch as the stability and solubility of the initiator are increased when chain extended. Polymerization is conducted in an anhydrous polar or non-polar solvent, such as tetrahydrofuran (THF), a hydrocarbon solvent, such as the various cyclic and acyclic hexanes, heptanes, octanes, pentanes, their alkylated derivatives, and mixtures thereof. The polymerization is preferably conducted in the absence of air.

The initiators prepared according to the present invention can be employed to polymerize any monomer that can be anionically polymerized. Useful monomers include conjugated diene monomers such as, but not limited to, 1,3-butadiene, 2,3-dimethyl-1,3-butadiene, 2-phenyl-1,3-butadiene, isoprene, 1,3-pentadiene, 2-methyl-1,3-pentadiene, 2,3-dimethyl-1,3-pentadiene, and 4,5-diethyl-1,3-octadiene. In one embodiment, the conjugated diene monomer are copolymerized with vinyl-substituted aromatic monomers such as, but not limited to, styrene, 4-methylstyrene, α-methylstyrene, 3,5-diethylstyrene, 4-propylstyrene, 2,4,6-trimethylstyrene, 4-dodecylstyrene, 2,3,4,5-tetraethylstyrene, 3-methyl-5-normal-hexylstyrene, 4-phenylstyrene, 2-ethyl-4-benzylstyrene, 3,5-diphenylstyrene, 1-vinylnaphthalene, 3-ethyl-1-vinylnaphthalene, 6-isopropyl-1-vinylnaphthalene, 6-cyclohexyl-1-vinylnapthalene, 7-dodecyl-2-vinylnaphthalene, and the like, and mixtures thereof.

In order to promote randomization in copolymerization and to control vinyl content, a polar coordinator may be added to the polymerization ingredients. Amounts range between 0 and 90 or more equivalents per equivalent of lithium. The amount depends on the amount of vinyl desired, the level of styrene employed and the temperature of the polymerization, as well as the nature of the specific polar coordinator (modifier) employed. Suitable polymerization modifiers include, for example, ethers or amines to provide the desired microstructure and randomization of the comonomer units.

Other compounds useful as polar coordinators are organic and include tetrahydrofuran (THF), linear and cyclic oligomeric oxolanyl alkanes such as 2,2-bis(2'-tetrahydrofuryl) propane, di-piperidyl ethane, dipiperidyl methane, hexamethylphosphoramide, N-N'-dimethylpiperazine, diazabicyclooctane, dimethyl ether, diethyl ether, tributylamine and the like. The linear and cyclic oligomeric oxolanyl alkane modifiers are described in U.S. Pat. No. 4,429,091, owned by the Assignee of record, the subject matter of which relating to such modifiers is incorporated herein by reference. Compounds useful as polar coordinators include those having an oxygen or nitrogen hetero-atom and a non-bonded pair of electrons. Other examples include dialkyl ethers of mono and oligo alkylene glycols; "crown" ethers; tertiary amines such as tetramethylethylene diamine (TMEDA); linear THF oligomers; and the like.

The amount of initiator employed in conducting anionic polymerizations can vary widely based upon the desired polymer characteristics. In one embodiment, it is preferred to employ from about 0.1 to about 100, and more preferably from about 0.33 to about 10 mmol of lithium per 100 g of monomer.

The anionic polymerizations can be quenched by employing several techniques that are well known in the art. In one technique, a terminator is added that may impart a functionality to the tail end of the polymer or that may serve as a coupling agent. Suitable terminators include, but are not limited to, metal halides, organic halides, alcohols, carboxylic acids, inorganic acids, sulfonic acid, water, and mixtures thereof. Some specific examples of preferred terminators include tin tetrachloride, tributyl tin chloride, silicon tetrachloride, trioctyl tin chloride, dioctyl tin dichloride, carbon dioxide, and epoxides.

The characteristics of the resultant polymer can vary greatly by employing techniques that are well known in the art. The molecular weight of the polymer ("base polymer") that is produced in this invention is optimally such that a proton-quenched sample will exhibit a gum Mooney ($ML_{1+4}$@100° C.) of from about 1 to about 150. In a preferred embodiment, the uncoupled polymer will have a number average molecular weight of from about 5,000,000 to about 1,000,000, and preferably from about 50,000 to about 300,000 as measured by using gel permeation chromatography (GPC) calibrated with polystyrene standards and adjusted for the Mark-Houwink constants for the polymer in questions. The molecular weight distribution of the polymer is preferably less than 2, more preferably less than 1.5, and even more preferably less than 1.3.

The functionalized polymers prepared with the initiators of this invention are particularly useful for use in preparing tire components. The functional polymers of this invention are particularly useful in preparing tire components. These tire components can be prepared by using the functional polymers of this invention alone or together with other rubbery polymers. Preferably, the functional polymers are employed in tread formulations, and these tread formulations will include from about 10 to about 100% by weight of the functional polymer based on the total rubber within the formulation. More preferably, the tread formulation will include from about 35 to about 90% by weight, and more preferably from about 50 to 80% by weight of the functional polymer based on the total weight of the rubber within the formulation. The preparation of vulcanizable compositions and the construction and curing of the tire is not affected by the practice of this invention.

In preparing the vulcanizable compositions of matter, at least one filler may be combined and mixed or compounded with a rubber component, which includes the functional polymer of this invention as well as other optional rubber polymers. Other rubbery elastomers that may be used include natural and synthetic elastomers. The synthetic elastomers typically derive from the polymerization of conjugated diene monomers. These conjugated diene monomers may be copolymerized with other monomers such as vinyl aromatic monomers. Other rubbery elastomers may derive from the polymerization of ethylene together with one or more α-olefins and optionally one or more diene monomers.

Useful rubbery elastomers include natural rubber, synthetic polyisoprene, polybutadiene, polyisobutylene-co-isoprene, neoprene, poly(ethylene-co-propylene), poly(styrene-co-butadiene), poly(styrene-co-isoprene), and poly(styrene-co-isoprene-co-butadiene), poly(isoprene-co-butadiene), poly(ethylene-co-propylene-co-diene), polysulfide rubber, acrylic rubber, urethane rubber, silicone rubber, epichlorohydrin rubber, and mixtures thereof. These elastomers can have a myriad of macromolecular structures including linear, branched and star shaped. Other ingredients that are typically employed in rubber compounding may also be added.

The rubber compositions may include fillers such as inorganic and organic fillers. The organic fillers include carbon black and starch. The inorganic fillers may include silica, aluminum hydroxide, magnesium hydroxide, clays (hydrated aluminum silicates), and mixtures thereof.

A multitude of rubber curing agents may be employed. For example, sulfur or peroxide-based curing systems may be employed. Also, see Kirk-Othmer, ENCYCLOPEDIA OF CHEMICAL TECHNOLOGY, $3^{rd}$ Edition, Wiley Interscience, New York 1982, Vol. 20, pp. 365-468, particularly VULCANIZATION AGENTS AND AUXILIARY MATERIALS pp. 390-402, or *Vulcanization* by A. Y. Coran, ENCYCLOPEDIA OF POLYMER SCIENCE AND ENGINEERING, $2^{nd}$ Edition, John Wiley & Sons, Inc., 1989, which are incorporated herein by reference. Vulcanizing agents may be used alone or in combination.

Other ingredients that may be employed include accelerators, oils, waxes, scorch inhibiting agents, processing aids, zinc oxide, tackifying resins, reinforcing resins, fatty acids such as stearic acid, peptizers, and one or more additional rubbers.

Preferably, the vulcanizable rubber composition Is prepared by forming an initial masterbatch that includes the rubber component and filler. This initial masterbatch is mixed at a starting temperature of from about 25° C. to about 125° C. with a discharge temperature of about 135° C. to about 180° C. To prevent premature vulcanization (also known as scorch), this initial masterbatch generally excludes any vulcanizing agents. Once the initial masterbatch is processed, the vulcanizing agents are introduced and blended into the initial masterbatch at low temperatures in a final mix stage, which does not initiate the vulcanization process. Optionally, additional mixing stages, sometimes called remills, can be employed between the masterbatch mix stage and the final mix stage. Rubber compounding techniques and the additives employed therein are generally known as disclosed in the in *The Compounding and Vulcanization of Rubber*, by Stevens in RUBBER TECHNOLOGY SECOND EDITION (1973 Van Nostrand Reinhold Company). The mixing conditions and procedures applicable to silica-filled tire formulations are also well known as described in U.S. Pat. Nos. 5,227,425; 5,719,207; 5,717,022, as well as EP 0890606, all of which are incorporated herein by reference.

Where the vulcanizable rubber compositions are employed in the manufacture of tires, these compositions can be processed into tire components according to ordinary tire manufacturing techniques including standard rubber shaping, molding and curing techniques. Typically, vulcanization is effected by heating the vulcanizable composition in a mold; e.g., it is heated to about 170° C. Cured or crosslinked rubber compositions may be referred to as vulcanizates, which generally contain three-dimensional polymeric networks that are thermoset. The other ingredients, such as processing aides and fillers, are generally evenly dispersed throughout the vulcanized network. Tire components of this invention preferably include tire treads. The rubber compositions, however, can also be used to form other elastomeric tire components such as subtreads, sidewalls, body ply skims, bead fillers and the like. Pneumatic tires can be made as discussed in U.S. Pat. Nos. 5,866,171; 5,876,527; 5,931,211; and 5,971,046, which are incorporated herein by reference.

In order to demonstrate the practice of the present invention, the following examples have been prepared and tested. The examples should not, however, be viewed as limiting the scope of the invention. The claims will serve to define the invention.

EXAMPLES

Example 1

Preparation of Cinnamyl-HMI

To a solution of hexamethyleneimine (HMI) (31 g, 0.3 mol) in cyclohexane, cinnamyl chloride (22.9 g, 0.15 mol) was added dropwise at room temperature with stirring. After 24 hours of agitation at 65° C., the amine chloride salt was filtered off and the resulting solution (cyclic-amino functionalized styryl compound) concentrated to a dark yellow oil. The product was purified by vacuum distillation (~1 mm Hg, 80° C.) to yield 22 g (68% yield). The structure was confirmed by $^1$H NMR analysis.

Preparation of Initiator

The BuLi-cinnamyl HMI initiator (chain extended) was prepared just prior to polymerization. A small amount of hexanes (61.6 g) was charged to a nitrogen purged reactor. Butyllithium (1.6 M, 8.5 mL) was added followed by cinnamyl-HMI (4.49 M, 2.73 mL) prepared above. Butadiene monomer (21.8% in hexanes, 23.4 g), which was used for chain extension, and a polar modifier (1.6 M, 1.02 mL) were charged last. This mixture was allowed to react with agitation at 50° C. for 1 hour and then used directly in the polymerization.

Reactor Batch Polymerization

The initiator prepared above was employed to polymerize poly(styrene-co-butadiene) in a batch polymerization. Specifically, a 5-Gallon reactor was charged with hexanes (5.95 lbs.), styrene (34% in hexanes, 3.11 lbs.), butadiene (21.8% in hexanes, 15.72 lbs.), and the BuLi-cinnamyl HMI initiator prepared above (13.6 mmol C—Li) were charged and the reactor was heated in batch mode to 50° C. and temperature peaked at 60° C., the mixture was stirred an additional 45 minutes and coupled with equal parts of tributyl tin chloride and tin tetrachloride. The resulting polymer was coagulated in isopropyl alcohol, antioxidant, drum-dried, and analyzed. The resultant polymer was analyzed for amine content and showed greater than 80% bound cyclic amine.

Reactor Semi-Batch Polymerization

The initiator prepared above was also employed in a semi-batch polymerization. A 5-gallon reactor was charged with hexanes (6.59 lbs.) and butyllithium-cinnamyl HMI initiator (13.6 mmol C—Li), which was prepared in a similar fashion to that described above. A mixture of styrene (34% in hexanes, 4.77 lbs.) and butadiene (21.87%, 13.42 lbs.) was added over a two-hour period to the 5-gallon reactor. The resulting cement was coupled with equal parts of tributyl tin chloride and tin tetrachloride as above and the final polymer analyzed. The resultant polymer was analyzed for amine content and showed greater than 80% bound cyclic amine.

Example 2

Preparation of Cinnamyl-O—$CH_2$-pyrene

To a solution of 1-pyrene methanol (5 g, 21.5 mmol) in THF (150 mL) was added NaH (2 g, 50 mmol). After stirring for 30 min., cinnamyl chloride (4.3 g, 28.7 mmol) was added drop wise. After 2.5 h of reflux, the reaction was quenched with water and the two layers separated. The organic solution was washed with water (2×100 mL), brine (2×100 mL), dried over $MgSO_4$ and concentrated to an orange oil. The product was purified by column chromatography (1:1, $CH_2Cl_2$:hexanes) to yield 5 g (67% yield). The structure was confirmed by $^1$H NMR analysis.

In situ Formation of Initiator and Subsequent Polymerization

The BuLi-Cinnamyl pyrene initiator was prepared in situ. A purged glass reactor (AKA bottle) was prepared in the standard fashion. Hexanes (54.6 g) and butadiene blend (22%, 45.6 g) were charged to the bottle followed by Buli (0.63 mL, 1.68 M) and cinnamyl-pyrene (0.8 mmol). The polar modifier (0.13 mL, 1.6 M) was charged last. This mixture was allowed to react with agitation at 50° C. for 1 h. After quenching with IPA and drying, the presence of the functional group was confirmed by $^1$H NMR.).

Example 3

Preparation of Cinnamyl-O-tetrahydropyran

A solution of cinnamyl alcohol (10.6, 19 mmol) and dihydropyran (7.3 g, 87 mmol) in dichloromethane (200 mL) was prepared. A catalytic amount of acid (p-toluene sulfonic acid) (20 mg) was added and the mixture stirred at room temperature under nitrogen for 4 hours. The reaction was diluted with a 5% sodium dicarbonate solution and the two layers separated. The aqueous layer was extracted once with diethyl ether (100 mL). The organic solutions were combined and washed with water (100 mL), brine (100 mL), dried over $MgSO_4$ and concentrated to a yellow oil. The product was pure as evidenced by $^1H$ NMR analysis (16 g: 93% yield).

In situ Formation of Initiator and Subsequent Polymerization

The BuLi-Cinnamyl-O-tetrahydropyran initiator was prepared in situ. A purged glass reactor (AKA bottle) was prepared in the standard fashion. Hexanes (54.6 g) and butadiene blend (22%, 45.6 g) were charged to the bottle followed by BuLi (0.63 mL, 1.68 M) and cinnamyl-O-tetrahydropyran (0.8 mmol). The polar modifier (0.13 mL, 1.6 M) was charged last. This mixture was allowed to react with agitation at 50° C. for 1 h. After quenching with IPA and drying, the presence of the functional group was confirmed by $^1H$ NMR.

Various modifications and alterations that do not depart from the scope and spirit of this invention will become apparent to those skilled in the art. This invention is not to be duly limited to the illustrative embodiments set forth herein.

What is claimed is:

1. A process for preparing a functionalized anionic polymerization initiator, the process comprising:

combining a functionalized styryl compound and an organolithium compound, where the functionalized styryl compound is defined by the formula X

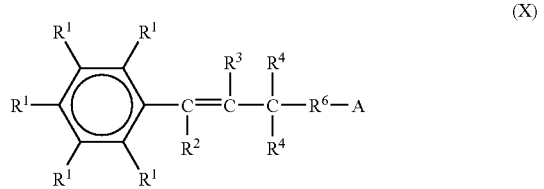

(X)

where each $R^1$ is independently hydrogen or a hydrocarbyl group, $R^2$ is hydrogen or a hydrocarbyl group, $R^3$ is hydrogen or a hydrocarbyl group, each $R^4$ is independently hydrogen or a monovalent organic group, $R^6$ is a covalent bond or a hydrocarbylene group, and A is a functional group.

2. An anionic polymerization initiator defined according to the formula I:

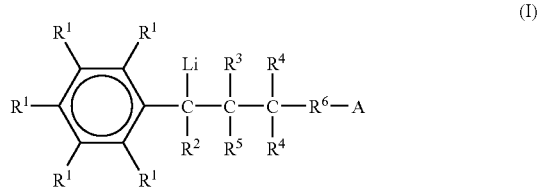

(I)

where each $R^1$ is independently hydrogen or a hydrocarbyl group, $R^2$ is hydrogen or a hydrocarbyl group, $R^3$ is hydrogen or a hydrocarbyl group, each $R^4$ is independently hydrogen or a monovalent organic group, $R^5$ is a hydrogen atom or a hydrocarbyl group, where at least one of $R^3$ or $R^5$ is hydrocarbyl, $R^6$ is a covalent bond or a hydrocarbylene group, and A is a functional group selected from the group consisting of amine groups, phosphines groups, ether groups, thio ether groups, seleno groups, silyl groups, alkyl tin groups, and short-chain thermoplastic polymer segments.

3. A polymer prepared by a process of comprising the steps of:

polymerizing monomer with an initiator that is prepared by combining a functionalized styryl compound and an organolithium compound, where the functionalized styryl compound is defined by the formula X

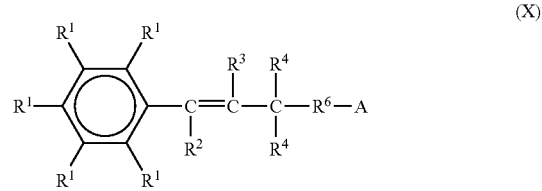

(X)

where each $R^1$ is independently hydrogen or a hydrocarbyl group, $R^2$ is hydrogen or a hydrocarbyl group, $R^3$ is hydrogen or a hydrocarbyl group, each $R^4$ is independently hydrogen or a monovalent organic group, $R^6$ is a covalent bond or a hydrocarbylene group, and A is a functional group.

4. The process of claim 1, where the functionalized styryl compound is N-(cinnamyl): -pyrrolidine, -3-methylpyrrolidine, -3,4-dimethylpyrrolidiene, -3,3-dimethylpyrrolidine, -piperidine, -4-methylpiperidine, -3-methylpiperidine, -morpholine, -4-methylpiperazine, -4-ethyl-piperazine, -4-propylpiperazine, -hexamethyleneimine, -trimethylperhydroazepine, -azacyclotridecane, -azacyclohexadecane, -azacycloheptadecene, -trimethylazabicycloöctane, -perhydroisoquinoline, or -perhydroindole.

5. The process of claim 1, where said step of combining combines about 0.8 mmol of the functionalized styryl compound with about 1.0 mmol of the organolithium compound.

6. The process of claim 1, where step of combining occurs in the presence of about 1 to about 20 mmol of monomer in order to chain extend the initiator.

7. The process of claim 1, where the functional group A is defined by the formula III

(III)

where each $R^9$ is independently hydrogen or a monovalent organic group and a is an integer from 4 to about 18.

8. The process of claim 1, where the functionalized styryl compound is prepared by combining a reactive styryl compound and a functionalized nucleophile.

9. The process of claim 1, where the functionalized styryl compound is prepared by combining a reactive styryl compound and a functionalized electrophile.

10. The polymer of claim 3, where the functionalized styryl compound is N-(cinnamyl): -pyrrolidine, -3-methylpyrrolidine, -3,4-dimethylpyrrolidiene, -3,3-dimethylpyrrolidine, -piperidine, -4-methylpiperidine, -3-methylpiperidine, -morpholine, -4-methylpiperazine, -4-ethyl-piperazine, -4-propylpiperazine, -hexamethyleneimine, trimethylperhydroazepine, -azacyclotridecane, -azacyclohexadecane, -azacycloheptadecene, -trimethylazabicycloöctane, -perhydroisoquinoline, or -perhydroindole.

11. The polymer of claim 3, where said step of combining combines about 0.8 mmol of the functionalized styryl compound with about 1.0 mmol of the organolithium compound.

12. The polymer of claim 3, where step of combining occurs in the presence of about 1 to about 20 mmol of monomer in order to chain extend the initiator.

13. The polymer of claim 3, where the functional group A is defined by the formula III

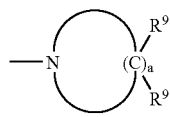

(III)

where each $R^9$ is independently hydrogen or a monovalent organic group and a is an integer from 4 to about 18.

14. The polymer of claim 3, where the functionalized styryl compound is prepared by combining a reactive styryl compound and a functionalized nucleophile.

15. The polymer of claim 3, where the functionalized styryl compound is prepared by combining a reactive styryl compound and a functionalized electrophile.

16. A process for preparing a functionalized anionic polymerization initiator, the process comprising:
combining a functionalized styryl compound and an organolithium compound, where the functionalized styryl compound is N-(cinnamyl): -pyrrolidine, -3-methylpyrrolidine, -3,4-dimethylpyrrolidiene, -3,3-dimethylpyrrolidine, -piperidine, -4-methylpiperidine, -3-methylpiperidine, -morpholine, -4-methylpiperazine, -4-ethylpiperazine, -4-propylpiperazine, -hexamethyleneimine, -trimethylperhydroazepine, -azacyclotridecane, -azacyclohexadecane, -azacycloheptadecene, -trimethylazabicyclooctane, -perhydroisoquinoline, or -perhydroindole.

17. The anionic polymerization initiator of claim 2, where the functional group A is an ether group defined by the formula

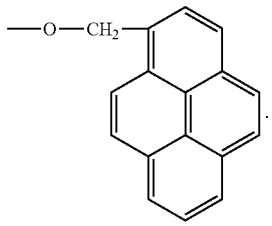

18. The anionic polymerization initiator of claim 2, where functional group A is a silyl group defined by the formula IX

(IX)

where each $R^{10}$ is independently selected from the group consisting of a hydrocarbyl group and an alkoxy group.

19. The anionic polymerization initiator of claim 18, where the functional group A is selected from the group consisting of trimethyl silyl, triethyl silyl, dimethoxy methyl silyl, and dimethyl methoxy silyl.

20. The anionic polymerization initiator of claim 2, where the functional group A is defined by the formula VII

(VII)

where $R^7$ is a hydrocarbyl group.

21. The anionic polymerization initiator of claim 2, where the functional group A is defined by the formula VIII

(VIII)

where $R^7$ is a hydrocarbyl group.

22. The anionic polymerization initiator of claim 2, where the functional group A is defined by the formula V

(V)

where each $R^7$ and $R^8$ is independently a hydrocarbyl group.

* * * * *